United States Patent

Kaiser

[11] Patent Number: 5,837,671
[45] Date of Patent: Nov. 17, 1998

[54] ORGANOLEPTIC COMPOUND AND COMPOSITION

[75] Inventor: Roman Kaiser, Uster, Switzerland

[73] Assignee: Givaudan-Roure (International) SA, Vernier-Geneve, Switzerland

[21] Appl. No.: 741,438

[22] Filed: Oct. 31, 1996

[30] Foreign Application Priority Data

Nov. 10, 1995 [CH] Switzerland ............... 3191/95

[51] Int. Cl.[6] ........................................ A61K 7/46
[52] U.S. Cl. ................... 512/26; 554/224; 426/650
[58] Field of Search .................. 512/26; 554/224; 426/650

[56] References Cited

U.S. PATENT DOCUMENTS

| 4,304,793 | 12/1981 | Naf et al. | 554/224 |
|---|---|---|---|
| 5,180,710 | 1/1993 | Naef et al. | 554/224 |

FOREIGN PATENT DOCUMENTS

| 0 009 632 | 4/1980 | European Pat. Off. | 512/27 |

OTHER PUBLICATIONS

M. Winter et al., "(Z)–4, 7–Octadiensäthylester und (Z)–Buttersäure–3, 5–hexadienyl–ester, zwei neue Aromastoffe der roten Passionsfrucht," *Helv Chim Acta*, vol. 62, No. 19, (1979), pp. 135–139.

M. Nagai et al., "Syntheses of Bicyclo[3.3.0]octanes via Bifurcating Radical Cyclization Pathways," *J. Org. Chem.*, 55, (1990), pp. 3440–3442.

*Primary Examiner*—James H. Reamer
*Attorney, Agent, or Firm*—George W. Johnston; Alan P. Kass; Mark E. Waddell

[57] ABSTRACT

Methyl (E)-4,7-octadienoate [(E)-4,7-octadienoic acid methyl ester] (1), as well as odorant and/or flavorant compositions containing compound (1) as an organoleptic active substance and the manufacture of compound (1).

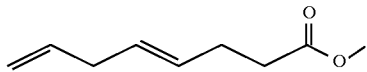

1

7 Claims, No Drawings

ORGANOLEPTIC COMPOUND AND COMPOSITION

FIELD OF THE INVENTION

The invention relates to the field of organoleptic (e.g., odorant and flavorant) compounds and compositions.

BACKGROUND

M. Nagai et al., 1990, J. Org. Chem., 55, 3440–3442, describe the ethyl ester of the formula

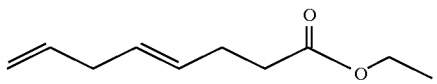

However, no reference is made to any olfactory properties.

Further, the compound ethyl (Z)-4,7-octadienoate of the formula

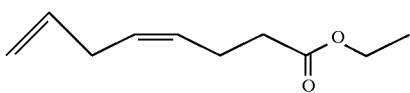

has been detected and synthesized by M. Winter et al., 1979 Helv. Chim. Acta, 62, No. 19 135–139, in the course of the isolation of flavoring substances of the red passion fruit (Passiflora edulis SIMS) by gas chromatography as a sensorially active trace component having a strikingly fruity odor with a fresh, succulent top note typical of pineapple. Compound 5 is, moreover, difficult to make because its synthesis is carried out via an exacting multi-stage synthesis.

SUMMARY OF THE INVENTION

In contrast thereto, the compound of the invention can be obtained in a simple manner by an orthoester rearrangement as described below. More particularly, the invention relates to the compound methyl (E)-4,7-octadienoate [(E)-4,7-octadienoic acid methyl ester] as well as to odorant and/or other compositions containing the compound as an organoleptic active substance and to the manufacture of the compound.

An object of the present invention is to provide a new organoleptically active substance. An additional object is to provide, in particular, an active substance which has a strong, fresh fragrance with fresh green-aldehydic aspects, and to compile odorant and/or flavorant compositions, especially of a flowery, flowery-fruity, fresh-flowery or green-fruity direction, using this active substance.

The aforementioned objects are achieved by methyl (E)-4,7-octadienoate.

DETAILED DESCRIPTION

The compound methyl (E)-4,7-octadienoate is novel and has the formula

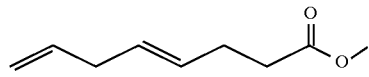

Methyl (E)-4,7-octadienoate (1) has a very strong and fresh fragrance which is dominated by green and aldehydic aspects.

The corresponding methyl ester of the formula

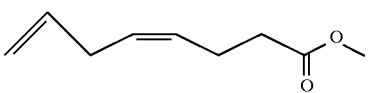

has not yet been described in the literature.

Having regard to these valuable olfactory properties, compound (1) is suitable as an odorant and/or flavorant, especially in combination with the extensive range of currently available natural and synthetic odorants and flavorants for the creation of perfume and flavorant compositions which can be used in all the customary fields of application. Examples of the numerous known odorant ingredients of natural or synthetic origin, whereby the range of natural raw materials can include not only readily-volatile but also moderately-volatile and difficultly-volatile components and that of synthetics can include representatives from several classes of substances, are:

Natural products, such as tree moss absolute, basil oil, agrumen oils (such as bergamot oil, mandarin oil, etc.), mastix absolute, myrtle oil, palmarosa oil, patchouli oil, petitgrain oil, wormwood oil, lavender oil, rose oil, jasmin oil, ylang-ylang oil and sandalwood oil, alcohols, such as farnesol, geraniol, linalool, nerol, phenyl-ethyl alcohol, rhodinol, cinnamyl alcohol, cis-3-hexanol, menthol and α-terpineol, aldehydes, such as citral, α-hexylcinnamaldehyde, hydroxy-citronellal, Lilial® (p-tert-butyl-α-methyl-dihydrocinnam-aldehyde), methylnonylacetaldehyde, phenylacetaldehyde, anisaldehyde and vanillin, ketones, such as allylionone, α-ionone, β-ionone, isoraldein (isomethyl-α-ionone), verbenone, nootkatone and geranyl-acetone, esters, such as allyl phenoxyacetate, benzyl salicylate, cinnamyl propionate, citronellyl acetate, decyl acetate, dimethylbenzylcarbinyl acetate, ethyl acetoacetate, ethyl acetylacetate, cis-3-hexenyl isobutyrate, linalyl acetate, methyl dihydrojasmonate, styrallyl acetate, vetiveryl acetate, benzyl acetate, cis-3-hexenylsalicylate, geranylacetate and the like, lactones, such as γ-undecalactone, δ-decalactone and pentadecan-15-olide, various components used in perfumery, such as indole, p-menthane-8-thiol-3-one, methyleugenol, eugenol and anethol.

The odorant compositions produced using compound (1), in particular those having a flowery or flowery-fruity direction, are particularly fascinating because of their originality.

Having regard to these olfactory properties, compound (1) is particularly suitable for co-use in the creation of the most diverse types of perfume. According to the invention, flowery and flowery-fruity compositions which are given a pleasant, very nature-like freshness by addition of compound (1), are a particularly important field of use, with the compositions being enriched to an increased extent by fruity and additionally by green aspects. However, compound (1) can also advantageously be used in other types of perfume, such as those having an oriental, woody or hesperidine-like base character, with the top note undergoing a valuable enrichment.

Compound (1) of the invention is also suitable for co-use in the creation of flavors, in particular generally of fruit flavors. Thus, for example, in flavors of the apple, peach, papaya, guava, kiwi, mango and banana type and in particular of the pear type, the green and fresh aspect are underlined very positively and in a natural manner.

Such flavors can be used, for example, for generating or improving, intensifying, increasing or modifying fruit flavors, for example, mango, peach and coconut. Possible fields of use of these flavors are, for example, foodstuffs, luxury consumables and drinks (finished foodstuff products).

The pronounced qualities of compound (1) enable it to be used as a flavorant in low concentrations. A suitable dosage comprises the range from 0.01 to 100 ppm, preferably from 0.1 to 10 ppm, in the finished product, i.e. the flavored foodstuff, luxury consumable or drink.

Compound (1) can be mixed with the ingredients used for flavoring compositions or added to such flavorings in the customary manner. Under the flavorings used according to the invention there are to be understood flavoring compositions which can be diluted or, especially in edible materials, dispersed in a manner known per se. They contain, for example, about 0.01–30 wt. %, especially in 0.1–10 wt. % of compound (1). They can be converted into the customary forms of use, such as solutions, pastes or powders according to methods known per se. The products can be spray dried, vacuum dried or lyophilized.

The known flavoring substances which are conveniently used in the production of such flavorings are either already referred to in the aforementioned compilation or can be taken from the literature, such as, for example, J. Merory, Food Flavorings, Composition, Manufacture and Use, Second Edition, The Avi Publishing Company, Inc., Westport, Conn. 1968, or G. Fenaroli, Fenaroli's Handbook of Flavor Ingredients, Second Edition, Volume 2, CRC Press, Inc. Cleveland, Ohio, 1975.

The following carrier materials, thickeners, flavor improvers, seasonings and auxiliary ingredients and the like, for example, also come into consideration for the production of such customary forms of use:

Gum arabic, tragacanth, salts or brewer's yeast, alginates, carrageen or similar absorbents; maltol, spice oleoresins or smoke aromas; cloves, diacetyl or sodium citrate; monosodium glutamate, disodium inosine 5'-monophosphate (IMP) or disodium guanosine 5-phosphate (GMP); or special flavoring substances, water, ethanol, propylene glycol, glycerol and the like.

Due to its pronounced olfactory properties, compound (1) is preferably suitable for use in luxury perfumes and cosmetics.

Methyl (E)-4,7-octadienoate (1) can be manufactured according to the invention from 1,5-hexadien-3-ol (2) by orthoester Claisen rearrangement with trimethyl orthoacetate (3) in the presence of a C1 to C8 carboxylic acid, in particular in the presence of propionic acid, in accordance with the equation:

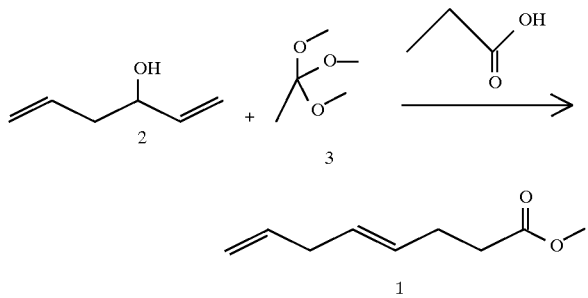

The 1,5-hexadien-3-ol (2) required as the starting material is known and is obtainable by a Grignard reaction from allylmagnesium bromide and acrolein using standard methods.

In the context of attempts at syntheses to give rise to the invention, some derivatives of methyl (E)-4,7-octadienoate (1) which have olfactory properties have also been synthesized, namely the compounds which are methyl(alkyl) homologues of compound (1) of the invention listed in Table 1 hereinafter.

TABLE I

| Compound | Odor |
| --- | --- |
| a) Methyl (E)-3-methyl-4,7-octadienoate | green, fatty, slightly fruity |
| b) Methyl (E)-4-methyl-4,7-octadienoate | fruity, fatty, fungoid |
| c) Methyl 3-ethyl-4-methyl-4,7-octadienoate | earthy, fungoid, green |
| d) Methyl (E)-3-propyl-4,7-octadienoate | singular, sweaty fruit note, overripe pears, not very pleasant |
| e) Methyl (E)-5-methyl-4,7-octadienoate | green, fruity, fatty |

Surprisingly, it has been found that none of the aforementioned compounds a) to e) has the outstanding properties of compound (1) of the invention, namely the fresh fragrance with fresh, green- aldehydic aspects. In the case of these compounds a) to e), the fatty, fungoid and sweaty olfactory aspects primarily cause trouble.

Further advantages, features and details of the invention will be evident from the following Examples.

EXAMPLES

The trivial names of individual components identified with * are listed in standard works in respect of their systematic chemical names: e.g. Allured's Flavor and Fragrance Materials—1996, Allured Publishing Corporation, Carol Stream, Ill., U.S.A. or S. Arctander, Perfume and Flavor Chemicals—1969, published by the author, Montclair, N.J., U.S.A.

1. Preparation of methyl (E)-4,7-octadienoate

Example 1

78.0 g (about 0.71 mol) of 1,5-hexadien-3-ol, obtained by a Grignard reaction from allylmagnesium bromide and acrolein, were dissolved in 198.0 g (1.65 mol) of trimethyl orthoacetate and 3.0 g (0.04 mol) of propionic acid were then added. The reaction mixture was heated to 120° C. and the methanol formed during the reaction was distilled off over a 15 cm Widmer column. After 2 hours, the reaction mixture was held at 130° C. for a further 1 hour to complete the reaction and was then cooled to room temperature, diluted with 500 ml of tert-butyl methyl ether and the solution was washed twice with 100 ml of saturated sodium bicarbonate solution, dried with sodium sulphate and concentrated. Distillation of the resulting 128 g of crude product over a 20 cm Widmer column gave 51.6 g of olfactorily good methyl (E)-4,7-octadienoate of boiling point 76° C./17 mbar and with a purity of about 98%.

Spectral data of the thus-prepared methyl (E)-4,7-octadienoate:

NMR (200 MHz, CDCl$_3$): 2.38 (m,4H); 2.73 (m,2H); 3.68 (s,3H); 4.97–5.07 (m,2H); 5.45 (m,2H); 5.70–5.90 (m,1H).
Mass spectrum: 154 (M+, 1), 122(6), 95 (23), 94 (36), 81 (36), 80 (89), 79 (100), 74 (38), 71 (14), 67 (34), 59 (24), 53 (30), 43 (46), 41 (64), 39 (49).

In Examples 2–8 hereinafter, the respective accord was smelt and compared in the usual manner using smelling strips. In addition, in Example 5 (flavorant) and the corresponding comparative Example 8, the foodstuff was tasted. Thereby, the same aspects were determined as on the smelling strips.

II. Formulation Examples

Example 2

Perfume composition with an oriental direction

|  | Composition | |
|---|---|---|
|  | (a) | (b) |
|  | (Parts by weight) | |
| Benzyl acetate | 30 | 30 |
| Linalyl acetate | 20 | 20 |
| p-tert-Butylcyclohexyl acetate | 80 | 80 |
| Phenylethyl acetate | 45 | 45 |
| α-Hexylcinnamaldehyde | 80 | 80 |
| Decanal 10% in DPG | 3 | 3 |
| 10-Undecenal 10% in DPG | 4 | 4 |
| 2-Methylundecanal 10% in DPG | 2 | 2 |
| Cyclamenaldehyde* | 5 | 5 |
| Bergamot oil, reconstituted | 85 | 85 |
| Sandalwood oil | 25 | 25 |
| Civet tincture, reconstituted 10% in DPG | 2 | 2 |
| Coumarin* | 25 | 25 |
| Cyclohexal* | 15 | 15 |
| Dihydromyrcenol* | 10 | 10 |
| Dodecenal 1% in DPG | 5 | 5 |
| Estragol 10% in DPG | 1 | 1 |
| Eugenol | 1.5 | 1.5 |
| Evernyl* | 1 | 1 |
| Galaxolid* 50% in DEP | 60 | 60 |
| Gardenol* | 8 | 8 |
| Geraniol | 30 | 30 |
| Hedione* | 5 | 5 |
| Indolene* | 1 | 1 |
| β-Ionone | 10 | 10 |
| Iso-E-super* | 5 | 5 |
| Isoraldein* 70 | 30 | 30 |
| Jasmone* | 1 | 1 |
| Lilial* | 40 | 40 |
| Linalool | 60 | 60 |
| Methyldiantilis* | 0.5 | 0.5 |
| Methyllaiton* 10% in DPG | 2 | 2 |
| Orange oil terpene, distilled | 80 | 80 |
| γ-Undecalactone | 3 | 3 |
| γ-Nonalactone | 5 | 5 |
| Rose oxide* 10% in DPG | 3 | 3 |
| Benzyl salicylate | 50 | 50 |
| Sandalore* | 35 | 35 |
| Stemone* | 5 | 5 |
| α-Terpineol | 15 | 15 |
| Vanillin | 10 | 10 |
| Vertofix* coeur | 50 | 50 |
| Dipropylene glycol | 52 | 44 |
| Compound (1) | — | 10 |
|  | 1000 | 1000 |

Perfume composition (a) was marked by an oriental character. The addition of 10 parts of compound (1) in perfume composition (b) imparted to this a pleasant, natural freshness and, surprisingly, the flowery aspect was advantageously underlined at the same time.

Example 3

Perfume composition with a fresh-flowery feminine direction

|  | Composition | |
|---|---|---|
|  | (a) | (b) |
|  | (Parts by weight) | |
| Benzyl acetate | 5 | 5 |
| Linalyl acetate | 80 | 80 |
| Phenylethyl alcohol | 20 | 20 |
| Methyl anthranilate 10% in DPG | 5 | 5 |
| Bergamot oil | 100 | 100 |
| Calone 1951* 10% in DPG | 5 | 5 |
| 1-carvone 10% in DPG | 2 | 2 |
| Cetalox* | 5 | 5 |
| Coumarin* | 3 | 3 |
| Cyclogalganate* | 3 | 3 |
| α-Damascone | 2 | 2 |
| Dihydromyrcenol* | 50 | 50 |
| Ebanol* | 5 | 5 |
| Evernyl* | 5 | 5 |
| Floralozone* 10% in DPG | 5 | 5 |
| Galaxolide* 50% in DEP | 110 | 110 |
| Geranium oil | 2 | 2 |
| Hedione* | 200 | 200 |
| cis-3-Hexenol | 1 | 1 |
| Indole* 1% in DPG | 2 | 2 |
| β-Ionone | 25 | 25 |
| Iso-E-super* | 45 | 45 |
| Jasmone* 10% in DPG | 8 | 8 |
| Lilial* | 20 | 20 |
| Linalool | 80 | 80 |
| Orange oil | 40 | 40 |
| Rosoflor 2* | 5 | 5 |
| cis-3-Hexenyl salicylate | 5 | 5 |
| Scentenal* 1% in DPG | 2 | 2 |
| Tropional* | 30 | 30 |
| Vertofix* coeur | 10 | 10 |
| Dipropylene glycol | 120 | 115 |
| Compound (1) | — | 5 |
|  | 1000 | 1000 |

Perfume composition (a) was marked by a fresh-flowery character and, considered overall, had a feminine effect. The addition of 5 parts of compound (1) in perfume composition (b) enlivened this by a pleasant freshness and made it appear fuller and more rounded. A pleasant green-fruity aspect furthermore manifested itself.

Example 4

Perfume composition with a fresh-flowery direction having green-fruity aspects

|  | Composition | |
|---|---|---|
|  | (a) | (b) |
|  | (Parts by weight) | |
| Benzyl acetate | 60 | 60 |
| Dimethylbenzylcarbinyl acetate | 25 | 25 |
| Geranyl acetate | 40 | 40 |
| Phenylethyl alcohol | 100 | 100 |
| α-Hexylcinnamaldehyde | 100 | 100 |
| 10-Undecenal | 0.3 | 0.3 |
| Phenylacetaldehyde | 2 | 2 |
| Bergamot oil, reconstituted | 100 | 100 |
| Cyclohexal* | 40 | 40 |
| Fixolide* | 70 | 70 |
| Geraniol | 50 | 50 |
| Clove oil | 7 | 7 |
| Hedione* | 50 | 50 |
| Heliotropin | 10 | 10 |

-continued

| Perfume composition with a fresh-flowery direction having green-fruity aspects | | |
|---|---|---|
| | Composition | |
| | (a) | (b) |
| | (Parts by weight) | |
| Isoeugenol | 2 | 2 |
| Isoraldein* 95 | 40 | 40 |
| Lilial* | 40 | 40 |
| Linalool | 50 | 50 |
| Mandarin oil | 20 | 20 |
| γ-undecalactone | 1 | 1 |
| Benzylsalicylate | 40 | 40 |
| cis-3-hexenylsalicylate | 10 | 10 |
| Tropional* | 10 | 10 |
| Dipropylene glycol | 132.7 | 129.7 |
| Compound (1) | — | 3 |
| | 1000 | 1000 |

Perfume composition (a) was dominated by a fresh-flowery note, but also had green-fruity aspects. The addition of 3 parts of compound (1) in perfume composition (b) enriched this by a pleasant, natural freshness and at the same time made it fuller and more elegant and emphasized a striking note which is reminiscent of pears and arouses interest.

Example 5

| Pear type flavor | | |
|---|---|---|
| | Composition | |
| | (a) | (b) |
| | (Parts by weight) | |
| Isoamyl acetate | 20 | 20 |
| Hexyl acetate | 40 | 40 |
| Geranyl acetate | 2 | 2 |
| Heptyl acetate | 5 | 5 |
| Ethyl butyrate | 10 | 10 |
| trans-2-hexenal | 5 | 5 |
| Amyl butyrate | 10 | 10 |
| Hexanol | 5 | 5 |
| Vanillin | 3 | 3 |
| Compound (1) | — | 4 |
| Propylene glycol | 900 | 896 |
| | 1000 | 1000 |

The addition of 4 parts of compound (1) to flavor (a) had a very advantageous effect by awakening the impression of a fully mature but nevertheless refreshing pear.

Such a flavor, i.e. flavor (b), was added to a finished foodstuff product, namely yoghurt, with compound (1) being present in a concentration of 0.1 to 100 ppm (as the concentrated base). The fully mature refreshing pear aspect was developed in full, in particular at a concentration of 0.1 to 10 ppm.

III. Comparative Examples

Example 6

When compound 1 was replaced in Example 2 by the same amount of compound 4, the attractive interaction between p-tert.-butylcyclohexyl acetate, phenylethyl acetate, stemone and compound 1, which was expressed in the composition by a very pleasant, natural freshness, was not achieved. The composition was much less developed in the top note.

Example 7

When compound 1 was replaced in Example 3 by the same amount of compound 4, this thus-modified perfume composition did not have the pleasant freshness produced with compound 1 and the desirable green-fruity aspect obtained with compound 1 was replaced by a substantially less attractive general fruity aspect.

Example 8

When compound 1 was replaced in Example 5 by compound 4, the fresh aspect was absent from the thus-obtained pear flavor.

In summary, it will be evident from the comparative Examples that compound 1 generally cannot be replaced by compound 4, because when this is done the desirable fresh aspect, which is often accompanied by green-fruity notes, is wholly absent.

I claim:

1. The olfactive compound methyl (E)-4,7-octadienoate of formula:

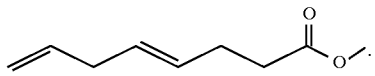

2. A method for enhancing organoleptic properties of an odorant and/or flavorant composition comprising including in said composition an organoleptically effective amount of methyl (E)-4,7-octadienoate (1).

3. An odorant and/or flavorant composition comprising methyl (E)-4,7-octadienoate (1).

4. The odorant and/or flavorant composition of claim 3, wherein the methyl (E)-4,7-octadienoate (1) is present in an amount of 0.1 to about 60 wt. %.

5. The odorant and/or flavorant composition of claim 3, wherein the methyl (E)-4,7-octadienoate (1) is present in an amount of 3 to 10 wt. %.

6. A finished foodstuff comprising 0.01 to 100 ppm of methyl (E)-4,7-octadienoate (1).

7. The finished foodstuff of claim 6, wherein the methyl (E)-4,7-octadienoate (1) is present in an amount of 0.1 to 10 ppm.

* * * * *